(12) United States Patent
Ehrenberg et al.

(10) Patent No.: US 6,518,040 B1
(45) Date of Patent: Feb. 11, 2003

(54) IN VITRO PRODUCTION OF PROTEINS BY TRANSLATION OF MRNA IMMOBILIZED ON A SOLID SURFACE

(76) Inventors: Mans Ehrenberg, S:t Olofsgatan 24, S-751 21 Uppsala (SE); Michail Pavlov, Kvarnbacksgatan 1, S-754 20 Uppsala (SE)

(*) Notice: Subject to any disclaimer, the term of this patent is extended or adjusted under 35 U.S.C. 154(b) by 0 days.

(21) Appl. No.: 09/423,418
(22) PCT Filed: Oct. 29, 1997
(86) PCT No.: PCT/SE97/01805
§ 371 (c)(1),
(2), (4) Date: Jun. 22, 2000
(87) PCT Pub. No.: WO98/21353
PCT Pub. Date: May 22, 1998

(30) Foreign Application Priority Data

Nov. 8, 1996 (SE) .................................. 9604108

(51) Int. Cl.[7] .................................. C12P 21/06
(52) U.S. Cl. ........................ 435/69.1; 435/183
(58) Field of Search ................ 435/69.1, 183

(56) References Cited

PUBLICATIONS

Samuel et al. Dynamics of Vlral mRNA Translation: Identification of Ribosome Pause Sites by Primer Extension Inhibition. Methods in Molecular Genetics (1994) 4:195–215.*

Dialog Information Services, file 154, Medline, Dialog accession No. 09317798, Medline accession No. 98013345, Pavlov MY et al: "Synthesis of region–labelled proteins for NMR studies by in vitro translation of column–coupled mRNAs"; & Biochimie (France) Jul. 1997, 79 (7) p415–22.

Biotechnology and Bioengineering, vol. 37, 1991, Eiry Kobatake et al, "Translation of Immobilized Genetic Information by Yeast Cell–Free Protein Synthesizing System" p. 723–p. 728.

FEBS Letters, vol. 57, No. 3, Oct. 1975, N.V. Belitsina, et al. "Isolation of Translating Ribosomes With a Resin–bound Poly–U Column" pp. 262–266.

Archives of Biochemistry and Biophysics, vol. 328, No. 1, Apr. 1996, Michael Yu. Pavlov, et al. "Rate of Translation of Natural mRNAs in an Optimized In Vitro System" pp. 9–16.

European Journal of Biochemistry, vol. 231, No. 1, Jul. 1995, Christophe Boutillon, et al. "Synthesis, three–dimensional structure, and specific [15]N–labelling of the streptococcal protein G B1–domain" pp. 166–180.

Methods in Enzymology—Nucleic Acids and Protein Synthesis—Part G, vol. LIX, 1979, V.I. Baranov, et al. "The Use of Columns with Matrix–Bound Polyuridylic Acid for Isolation of Translating Ribosomes" pp. 382–397.

Methods in Enzymology—Nucleic Acids and Protein Synthesis—Part H, vol. LX, 1979, N.V. Belitsina, et al. "Translation of Matrix–Bound Polyuridylic Acid by *Escherichia coli* Ribosomes" pp. 745–760.

* cited by examiner

*Primary Examiner*—Ponnathapu Achutamurthy
*Assistant Examiner*—Kathleen Kerr
(74) *Attorney, Agent, or Firm*—Stephen G. Ryan; Royal N. Ronning, Jr.

(57) ABSTRACT

An in vitro method for production of a protein (polypeptide), characterised in that the mRNA encoding the protein is translated when bound to a solid phase. By allowing for a pause at a terminating stop codon and addition of release factor the final proteon may be obtained in almost pure form. By allowing for pauses and restart at internal codons and replacement of the amino acid mixture used before a pausing with an amino acid mixture that differs with resect to labelling, region-labelled polypeptides/proteins can be accomplished. A labelled polypeptide/protein, characterised in that its amino acid sequence contains one or more regions of two or more labelled amino acid residues in sequence. In a subaspect, the polypeptide/protein has at least one amino acid that is occurring twice and this amino acid differs in labelling at least two positions.

5 Claims, 4 Drawing Sheets

SEQUENCE LISTING

<160> NUMBER OF SEQ ID NOS: 5

<210> SEQ ID NO 1
<211> LENGTH: 72
<212> TYPE: DNA
<213> ORGANISM: artificial sequence
<220> FEATURE:
<223> OTHER INFORMATION: synthetic oligonucleotide

<400> SEQUENCE: 1
gaaattaata cgactcacta tagggttaac tttagtaagg aggtaaaaaa aatgaaactg      60
tgcctggtgt gc                                                          72

<210> SEQ ID NO 2
<211> LENGTH: 59
<212> TYPE: DNA
<213> ORGANISM: artificial sequence
<220> FEATURE:
<223> OTHER INFORMATION: synthetic oligonucleotide

<400> SEQUENCE: 2
tttttttttt tttttttttt tctgcagctg ctactgtatt cctttattt ttttctttg       59

<210> SEQ ID NO 3
<211> LENGTH: 54
<212> TYPE: DNA
<213> ORGANISM: artificial sequence
<220> FEATURE:
<223> OTHER INFORMATION: synthetic oligonucleotide

<400> SEQUENCE: 3
gaaattaata cgactcacta tagggttaac tttagtaagg aggtaaaaaa aatg           54

<210> SEQ ID NO 4
<211> LENGTH: 46
<212> TYPE: PRT
<213> ORGANISM: artificial sequence
<220> FEATURE:
<223> OTHER INFORMATION: synthetic peptide

<400> SEQUENCE: 4

Met Lys Leu Cys Leu Val Cys Ser Asp Glu Ala Ser Gly Cys His Tyr
1               5                   10                  15

Gly Val Leu Thr Cys Gly Ser Cys Lys Val Phe Phe Lys Arg Ala Val
                20                  25                  30

Glu Gly Gln His Asn Tyr Leu Cys Ala Gly Arg Asn Asp Cys
            35                  40                  45

<210> SEQ ID NO 5
<211> LENGTH: 38
<212> TYPE: PRT
<213> ORGANISM: artificial sequence
<220> FEATURE:
<223> OTHER INFORMATION: synthetic peptide

```
-continued

<400> SEQUENCE: 5

Ile Ile Asp Lys Ile Arg Arg Lys Asn Cys Pro Ala Cys Arg Tyr Arg
1               5                   10                  15

Lys Cys Leu Gln Ala Gly Met Asn Leu Glu Ala Arg Lys Thr Lys Lys
            20                  25                  30

Lys Ile Lys Gly Ile Gln
        35
```

IN VITRO PRODUCTION OF PROTEINS BY TRANSLATION OF MRNA IMMOBILIZED ON A SOLID SURFACE

TECHNICAL FIELD

The present invention concerns, firstly, solid phase translation in general of mRNA to give a protein (polypeptide), encoded by the mRNA, and secondly, as a subaspect, region specific labelling of one or more predetermined regions (part sequences) of a polypeptide chain (protein) by solid phase translation of mRNA in vitro. The invention also encompasses novel region specific labelled proteins/polypeptides. The labelled polypeptides have their primary use in structural studies by NMR.

TECHNICAL BACKGROUND

The inventive method generalises an earlier mRNA-analogue (poly (U)) column translation method (Belitsina et al, 1975; Belitsina and Spirin, 1979) refined by Baranov et al., (1979), used to obtain ribosome in pre- and post-translocational states. Poly (U) as used in this earlier technique is not mRNA since it does not contain all the elements necessary for normal translation (stop codon, SD-sequence, (Shine-Delgarno sequence), ribosome binding site etc). Homopolymers of amino acids are not proteins. In the context of the invention homo polymers of amino acids are also excluded from the concept of polypeptides. In vitro translation has been described previously (e.g. Pavlov and Ehrenberg, 1996, and Ehrenberg et al, 1990).

NMR spectroscopy has over the past decade become a very powerful method to determine structures of small proteins in solution (Bax, 1989; Schwabe et al, 1990; Härd et al, 1990; Baumann et al, 1993; van Tilborg et al, 1995). NMR has the intrinsic limitation that, as the studied proteins get larger, there is a drastic reduction in the resolution of their NMR spectra (Bax, 1989). This drawback has been partially overcome by the application of various isotope labelling strategies (Muchmore et al, 1989; Ramesh et al, 1994). At the same time, there is still a pronounced upper limit around 30 kD for the determination of protein structures at high resolution using NMR spectroscopy (Bax, 1989).

One may identify three major types of isotope labelling strategies for NMR studies. The first is "uniform" labelling, where all the different amino acids in a polypeptide are labelled with, e.g., $^{15}N$, $^{14}C$ or $^{2}H$ isotopes. A combination of $^{15}N$, $^{14}C$ or $^{2}H$ "uniform" labelling recently made it possible to determine the structure in solution of such a large molecular complex as the trp repressor in complex with operator DNA (Zhang et al, 1994).

A second strategy is "selective" isotope labelling of proteins. This means that only a limited class of isotope labelled amino acids are built into the polypeptide, while the other amino acids are unlabelled. Selectively labelled proteins are obtained from over-producing bacterial strains, which grow in media where one or several types of amino acids are isotope labelled. This strategy has become very useful for structural analysis with NMR (Muchmore et al, 1989; Ramesh et al, 1994 and references therein).

A third strategy, which we denote "region specific" labelling, is more difficult to implement technically. This strategy means that labelled amino acids are incorporated only in one or more predetermined regions. One or more of all amino acid residues of a given peptide region may be labelled, while amino acids located outside the region may be unlabelled. We judge this, third strategy as the potentially most powerful way to extend the range of NMR-spectroscopy beyond the 30 kD limit to larger protein structures and complexes.

One way to obtain region specific labelling of proteins is by chemical polypeptide synthesis (Boutillon et al, 1995). At present, this method can only be used for small proteins.

OBJECTIVE OF THE INVENTION

A first objective is to provide an improved general method for in vitro translation enabling direct production of proteins in almost pure form.

A second objective is to provide a general method for region specific labelling of proteins based on in vitro translation as described e.g. by Pavlov and Ehrenberg, 1996, and Ehrenberg et al, 1990.

A third objective is to apply the solid support translation technology of the invention for implementing synthesis of region labelled proteins.

A fourth objective is to provide proteins that are isotope labelled at one or more predetermined regions.

The Invention

These objectives can be accomplished by a method that contemplates translation of real mRNAs stably linked to a solid phase to give real proteins polypeptides). These mRNAs contain in frame codons to be translated to an amino acid sequence. For procaryotes they also contain a Shine and Dalgarno sequence, a ribosomal binding site, an initiation codon and a termination codon, but one or several of these additional features may be deleted. For eucaryotes there is normally a cap structure at the 5'-end of the mRNA. One major advantage of this technique is that the ribosomes can be stalled at the stop codon that signals that the protein is full length (i.e., a terminating stop codon) as long as release factor is not included in the translation mixture. Subsequently, all components and factors necessary for translation can be rinsed off the solid phase in a simple way. After this step the solid phase linked mRNAs hold the ribosomes which hold the peptidyl-tRNAs that contain the protein of interest. Addition of the appropriate release factor (RF1 for UAA, UAG and RF2 for UAA or UGA) hydrolyses peptidyl-tRNA removing the protein of interest from the ribosomes that remain immobilized on the solid phase. Another rinsing step elutes the protein of interest together with catalytic amounts of RF1/2, making the final purification very simple.

Accordingly, the inventive method for production of proteins (polypeptides), is characterized in that mRNA encoding a protein of interest and bound to a solid phase is translated in vitro. In order to be able to obtain a highly purified form of the protein directly from the column translation is preferably done in two steps: first with a translation mixture containing all components for translation to a terminating, stop codon but devoid of the appropriate release factor activity—removal of the translation mixture—addition/introduction of the appropriate release factor activity.

A complete translation mixture is normally in the form of an aqueous buffer solution and allows for translation of the complete mRNA of interest and release of the so expressed protein from the tRNA—ribosome—mRNA complex. The mixture thus contains all ingredients necessary for translation, i.e. ribosomes, amino acids, amino acyl tRNA synthetases, tRNAs, initiation factors, elongation factors, energy giving system, buffering substances etc. See for instance the experimental part and references cited therein.

The exact composition will depend on the origin of the various enzymes and factors utilized. For an *E. coli* origin, for instance, specific components, such as fmet-tRNA$^{fmet}$, may have to be included.

By manipulating the translation mixture, translation may be paused and restarted at predetermined positions of the mRNA. The translation mixture may be added step-wise to the mRNA to be translated, such as a first portion (mixture) comprising ribosomes, initiation factors and for a procaryotic system fmet-tRNA$^{fmet}$ (for an eucaryotic system the initiator is met-tRNA$^{met}$) (initiation mix) followed by a second portion (mixture) comprising elongation factors, amino acyl tRNA synthetases, transfer RNAs, amino acids, energy giving system etc (translation mix). In the preferred case the translation mixture is added stepwise with mixes varying in composition enabling pausing and restarting of translation at predetermined and well-defined positions.

A pause in translation may be achieved by eliminating from a mixture the amino acyl-tRNA activity that reads the codon, where the translating ribosome shall stop. This may be achieved by removing the corresponding amino acid from the translation mixture, preferably in conjunction with a defective tRNA synthetase activity for that amino acid. Alternatively, the pausing may be at an internal stop codon in the mRNA. Readtbrough of the internal stop codon is achieved by introducing suppressor tRNA activity that is specific for the internal stop codon, by adding suppressor tRNA changed with the correct amino acid at that position in the polypeptide sequence. Still another alternative for creating a pause at a defined codon is to use a mix which is lacking the isoacceptor tRNA activity for that codon. As indicated above it is often preferred to use two alternatives in conjunction for pausing at a desired codon. Restart is accomplished by addition/introduction of the lacking activity (activities).

By arranging for pausing at two or more internal codons, it is possible to define internal regions that can be translated specifically in the presence of a desired labelled amino acid mixture.

By running the translation before and after a pause with mixtures containing amino acids differing in labelling, region specific labelled proteins (polypeptides) will be obtained. A specifically labelled region may contain two or more amino acid residues in sequence. The maximal length of a region is the total length of the protein (polypeptide) produced minus one or two amino acid residues. Specifically labelled regions of one amino acid residuess may be better obtained by methods not belonging to the invention.

The label may be of any type provided it is compatible with translation. This in most cases means that the label is an isotope of one or more of the basic elements normally occurring in native amino acids, i.e. an isotope of N, C, O, H and S, that may be either radioactive (e.g. $^3$H, $^{35}$S, $^{14}$C) or non-radioactive (e.g. $^{15}$N, $^{13}$C, $^2$H). Isotope labelling includes cases where a larger part of the protein (polypeptide) contains a "non-normal" isotope (e.g. $^2$H (deuterium)) while the region of interest contains the "normal" isotope (e.g. $^1$H (protons). Labelling with isotopes means that the labelled amino acid carries more than normal amounts of the isotope concerned.

In one preferred mode of the "labelling" aspect of the invention, the mRNA encoding the polypeptide to be produced is contacted with a first translation mix A that permits translation but is deficient in at least one of the above-mentioned activities responsible for readthrough of a codon at which pausing is desired. In a subsequent step the nascent polypeptide ribosome-mRNA-solid phase complex is contacted with a second translation mix B that permits readtbrough of the codon at which the translation previously had stopped for mix A. Readthrough can be accomplished by including in mix B the activity/activities causing the pausing for mix A. In analogy with mix A, mix B can be deficient in a component specific for a predetermined amino acid encoding codon or for an internal stop codon (downstream the pausing position for mix A), which means that translation in conjunction with mix a will be halted at this second predetermined codon. Optionally, mix B may be replaced with further translation mixes (C, D, and so on), such that a subsequent mix permits restarting of translation from a predetermined codon at which the translation is paused for the closest preceding mix. By allowing the amino acid compositions for juxta-positioned translation mixes to differ with respect to labelling of one or more amino acids, region specific labelling may be achieved in any preselected region/regions of interest in a protein. By providing release factor (RF1 and RF2) adapted to the terminating stop codon used (UAA, UAG, UGA) the completed polypeptide will be released from the tRNA-ribosome-mRNA complex attached to the solid phase.

The temperature is selected according to rules known in the art, which normally means 10–40° C. for systems derived from eubacteria or eucaryotes, bearing in mind that a too low temperature will give a slow translation and a too high temperature will result in denaturation and inactivation of the enzymes and other proteins involved. For systems derived from archaebacteria consideraly higher temperatures may be used. The pH conditions are also selected as outlined in the art for translation in vitro.

The solid phase used (support, carrier) are as a rule of the same type as those used as chromatographic adsorbents or supports for solid phase synthesis of oligo and poly nucleotides/peptides and encompass particulate as well as monolithic material, all of which in the preferred form should exhibit a hydrophilic contact area towards the liquid medium used. The support may be porous or non-porous. The link between the solid support and the mRNA may be of any type as long as it can withstand the conditions applied during translation/initiation and is compatible with efficient translation. Preferably the link is of covalent nature, for instance by attachment to the support via a terminal part, preferably a non-coding spacer sequence, of the mRNA, with preference for the 3'-end of the mRNA. Potential alternative ways of linking mRNA to supports involve attachment of affinity ligands to terminal parts of mRNA in combination with complementary receptors attached to the support. Biotin-streptavidin and anti-hapten high affinity antibodies are interesting ligand-receptor pairs that can be used.

Solid phase bound mRNA may also be a consequence of transcribing solid phase bound DNA encoding the protein/polypeptide of interest (e.g. cDNA). In this type of binding one may start amplifying target DNA by PCR using two primers one of which is biotinylated. The amplified biotinylated DNA is then transferred to a streptavidine coupled solid phase where it becomes firmly bound to the solid phase through a streptavidine-biotin complex. The DNA is then transcribed by an RNA polymerase to prepare mRNA. mRNA is retained in complex with the RNA polymerase used and the DNA and can be translated in the same manner as for mRNA directly bound to the solid phase.

The main advantage with mRNA-linked solid supports is that a nascent or finished polypeptide, still linked to peptidyl-tRNA ribosome and mRNA, can easily be separated from all other components in a translation mix by simple washing. This makes switching between labelled and unlabelled amino acids easy, and gives almost pure protein in the final elution step.

After the complete translation and release of the polypeptide from the ribosome, the polypeptide should be isolated and purified. This can be done by techniques well known in the art, bearing in mind that the use of solid supports carrying the mRNA to be translated is very advantageous for quickly obtaining a highly purified labelled polypeptide.

One aspect of the invention comprises a labelled polypeptide/protein characterized in that its amino acid sequence contains one or more regions of two, three or more labelled amino acid residues in sequence. The label is preferably an isotope as described above. The two or more labelled amino acids that are in sequence may be the same or different. By region is meant part sequences of two or more amino acids situated at chosen places in the sequence of the full length polypeptide/protein. The labelled part sequence may extend up to the full length protein although in order to be called a part sequence at least one or more amino acid must be missing. In a subaspect of this aspect, at least one amino acid is occurring at least twice, with the provision that the labelling of such an amino acid differs in at least two positions.

The best mode of the invention at the filing date is presented in the Experimental Part.

EXPERIMENTAL PART

Materials and Methods

General Description of the Technique

Synthesis of region labelled proteins involved the following consecutive steps:

a) An initiation mix, containing ribosomes, initiation factors and precharged fMet-tRNA$^{fMet}$, is applied to a column with mRNAs 3'-covalently coupled to a solid support.

b) A translation mix, containing an energy regenerating system (Jelenc and Kurland, 1979), elongation factors, tRNA synthetases, bulk tRNA and unlabelled amino acids, is applied to the column. The ribosomes, initiated in step (a), translate the column coupled mRNA to the first codon of the region of interest, where they pause.

c) The first translation mix is washed out from the column and a second translation mix, containing labelled amino acids, is applied. The ribosomes translate to the last codon of the region of interest, where they pause again.

d) The second translation mix is washed out and a third translation mix containing unlabelled amino acids, is added to the column and the ribosomes translate the mRNA to a termination STOP codon, where they pause.

e) The third translation mix is washed out from the column, release factor is applied and almost pure region labelled protein is eluted.

Chemicals

Phosphoenol pyruvate, putrescine, spermidine, myokinase and non-radioactive amino acids were from Sigma (U.S.A.). Pyruvate kinase was from Boehringer (Germany). All radioactive chemicals were from Amersham (United Kingdom). Other chemicals of analytical grade were from Merck, USA. Adipic acid Hydrazide Agarose was from Pharmacia Biotech AB (Uppsala, Sweden).

General Components Used in the Translation System.

Initiation factors were purified from overproducing strains according to Soffientini et al (1994) with minor modifications. Elongation factors Tu, Ts and G were purified according to Ehrenberg et al (1990). Bulk tRNA was prepared according to Kelmers et al (1971). Ribosomes were purified from E. coli strain 017 (Zengel et al, 1977) according to Jelenc (1980) and stored in polymix buffer (Jelenc and Kurland, 1979) at −80° C. tRNA$^{fMet}$ was isolated from bulk E. coli tRNA as described by Seno et al (1968). Acylation and formylation of tRNA$^{fMet}$ were according to Dubnoff and Maitra (1971). [$^3$H]Met-tRNA was purified to near 100% on BD-cellulose and the final degree of formylation was 80%. Release factor RF1 was purified from an overproducing strain as for initiation factors Crude synthetase mixtures (denoted RS30) were prepared from the S30 supernatant from E. coli cells. The supernatant was first applied to a DEAE-Sepharose CL 6B column in TM buffer [40 mM Tris (pH 7.5); 5 mM MgCl$_2$; 2 mM DTE; 10% glycerol; 100 mM PMSF; 0.02% NaN$_3$] and then eluted with a 0–500 mM NaCl gradient in the same buffer. The synthetase containing fractions starting from GlnRS and ending with LysRS, were pooled, precipitated with ammonium sulphate, dialysed against polymix buffer and stored at −20° C. after addition of glycerol (50% final concentration).

Four different synthetase mixtures were used:

(a) mixture RS30WT, purified from MRE600 (wt) E. coli cells.

(b) mixture RS30-ThrRS, purified from strain IBQC6111 (Corner et al, 1996, and references cited therein), with a deficient ThRS.

(c) mixture RS30-GlnRS, purified from strain IBPC420 (Corner et al, 1996, and references cited therein), with a deficient (temperature sensitive) GlnRS.

(d) mixture RS30-RF1, purified from strain MRA8 (Zang et al, 1994) with a deficient release factor RF1.

Construction of a modified GR DBD gene and preparation of mRNA for GR DBD: An artificial gene, GR8UAG, for the DNA binding domain (DBD) of the human glucocorticoid receptor (GR) was derived by PCR technique using the forward primer (5')
gaaattaatacgactcactatagGGTAACTTTAgtAAGGAGg
Taaaaaaa ATGAAACTGTGCCTGTgTGC

SEQ ID NO 1 and the reverse primer (5')
ttttttttttttttttttttCTGCAGgctactgTattCCTTTTATTTT
TTTCTTTG

SEQ ID NO 2

The plasmid pT7GR8 (obtained from Anthony Wright) which contains the coding sequence of GR DBD was used as a template (sequences of the primers complementary to the plasmid sequences are underlined). The resulting artificial gene contained a promotor for T7 RNA polymerase, a ribosome binding site (RBS) with the epsilon chain (Olins et al., 1989) and a strong Shine-Dalgarno (SD) sequence (Gold et al., 1990):

gaaattaatacgactcactatagGGTTAACTTTAgtAAGGAGg
TaaaaaaaATG

T7 promotor epsilon SD-Sequence

SEQ ID NO 3 derived from the forward primer. The gene also contained a poly(A) tail, derived from the reverse primer. In addition the original ochre terminating stop codon UAA in the plasmid sequence of GR DBD was substituted with an amber terminating stop codon (shown in bold face type in the reverse primer sequence (SEQ ID NO 2)), read by release factor RF1 but not by RF2. The poly(A) tail simplifies isolation of full length mRNA transcripts (below).

The reaction mix (4 ml) for in vitro transcription contained 40 mm Tris (pH 7.9), 22 mM MgCl$_2$, 2 mM spermidine, 2 mM DTE; 4 mM each of ATP, UTP, CTP, and GTP, 150 pmol GR8UAG, 100 units RNAguard (Pharmacia Biotech AB) and 2000 units T7 RNA polymerase. After 3 h incubation at 37° C. the reaction was stopped by addition of NaCl and EDTA to the final concentrations of 0.5 M and 20 mM, respectively. The mix was subsequently cooled, diluted with buffer A [10 mM Tris (pH 7.5), 500 mM NaCl, 1 mM EDTA] and applied to a 2 ml oligo(dT) cellulose column (Pharmacia Biotech AB). Non-bound material was removed from the column by washing with buffer A and GR8UAG mRNA was eluted with buffer A lacking NaCl.

Preparation of mRNA resin and column translation. 1.5 nmol of Gr8UAG mRNA was incubated for 1 h in he dark at room temperature in 1.0 ml of 100 mM NaOAc (pH 5.1) buffer with 10 mM freshly prepared sodium metaperiodate (NaIO$_4$). The oxidised mRNA was ethanol precipitated, the pellet was washed with 80% ethanol and re-dissolved in 1.0 ml of 100 mM acetate buffer (pH 5.1). Finally, the pellet was dissolved in 1 ml of 100 mM H$_2$O and passed through a NAPD10 column (Pharmacia Biotech AB) equilibrated with H$_2$O to remove traces of NaIO$_4$. Adipic Acid Hydrazide Agarose (Pharmacia Biotech AB) was washed extensively with water. The resin (4 ml) was then resuspended in 10 ml of 200 mM sodium acetate (pH 5.1) and 1.5 ml of oxidised GR8UAG mRNA from the NAPD10 column was subsequently added. The coupling reaction (spontaneous coupling) was allowed to proceed for 20 h at 6° C. with mild shaking. Then, an equal volume of pure glycerol was added to the resin (now denoted mGRU8UAG), which subsequently was stored at −20° C. From the OD of the column wash, it was estimated that more than 90% of the applied mRNA was coupled to the resin.

To prepare a column for translation, 2 ml of mGRU8UAG resin was transferred into a Poly Prep Chromatography column (BioRad, USA). The column was washed with 8 ml water, then with 10 ml of 2 M KCl and finally with 8 ml water, to remove gycerol and unbound material. Before each translation experiment, the column was pre-equilibrated with polymix buffer (see below) containing 1 mM GTP. The OD was monitored to detect mRNA dissociation. The final bed volume of the column was 0.4 ml and the calculated density of mRNA was 0.35 nmol/ml. The total amount of mRNA in the column was 140 pmol.

Mixes for Translation Experiments.

All mixes described were prepared on ice in polymix buffer (Jelenc and Kurland, 1979; Wagner et al, 1982). Polymix buffer contained, at working strength, 5 mM magnesium acetate, 5 mM potassium phosphate (pH 7.3), 95 mM potassium chloride, 5 mM ammonium chloride, 0.5 mM calcium chloride, 1 EM spermidine, 8 mM putrescine and 1 mM 1,4-dithioerythritol (DTE).

Initiation mixes. These contained 1 mM GTP, 0.5 unit/ml RNA guard (Pharmacia Biotech AB) as well as different amounts of 70S ribosomes, initiation factors IF1, IF2, IF3 and fMet-tRNA$^{fMet}$ as specified for each experiment, but always with the molecular ratios 2(Rib):3(IF1):2(IF2):3 (IF3):3(fMet-tRNA$^{fMet}$). Different translation mixes were used to prepare a region labelled GR DBD. They all contained 45 μM EF-Tu, approximately 60 μM of bulk tRNA (estimated from OD at 260 nm), 4,5 μM EF-G, 2 μM EF-Ts, 1 mM ATP, 10 mM phosphoenolpyruvate, 0.8 mM GTP, 0.2 mM CTP, and also (per 100 ml) 5 μg pyruvatekinase (PK), 0.3 μg myokinase (MK), 0.2 OU (at 280 nm) of the corresponding RS30 synthetase mix. Concentrations of added amino acids were as specified in each experiment.

Translation mixes for column translations. To synthesise in the column a region labelled domain of glucocorticoid receptor (GR DBD) three translation mixtures were prepared. Mix A (TMA) contained RS30 synthetase mix with defective ThrRS and also all unlabelled amino acids except Thr and Trp at 0.1 mM concentration. Mix B (TMB) contained RS30 synthetase mix with defective GlnRS and nine $^{14}$C labelled amino acids: A,E,F,G,K,R,S,T and V with a specific activity of approximately 1500 dpm/pmol at approximately 5 μM concentration each. Mix C (TMC) contained RS30 sythetase mix with defective RF1 and all unlabelled amino acids except Trp at 0.1 mM concentration. All translation mixtures were pre-incubated 10 min at 39° C. before they were applied to the mRNA-column.

Gel Electrophoresis and Data Acquisition.

Samples for SDS-gel electrophoresis were incubated for 30 min at 42° C. in 0.2 M freshly prepared NaOH to hydrolyse peptidyl- and aminoacyl-tRNAs. The column-eluted samples were concentrated to 20 μl by vacuum-evaporation. Subsequently, free SH-groups were blocked by addition of iodoacetamide to 0.1 M final concentration. Then an appropriate volume of 5 times concentrated electrophoresis buffer (Schagger and von Jagow, (1987) was added to the samples and they were heated to 70° C. for 5 min and applied to the gel.

A gel system for SDS-gel electrophoresis (Schagger and von Jagow, 1987), resolving polypeptides between 1 and 100 kD, was used to analyse the translation products. Gels (0.5 mm thick) were run at room temperature overnight at 100 V. Gels were quantified with Phoshor-Imager instrument (Molecular Dynamics). [$^{14}$C]-Rainbow low weight protein markers (Amersham, U.K.) from 2.2 to 46 kD were used to estimate the molecular weights of the gel bands.

Band-shift Assay

The binding of synthesised GR DBD to a target was analysed by a band shift assay (Dahlman-Write et al, 1990).

Results

In the present work we have labelled the DNA recognising helix of the DNA binding domain (DBD) of the human glucocorticoid receptor (GR DBD) (Härd et al., (1990) and Dahlman-Wright et al., (1990)). The DNA recognising helix is flanked by the first threonine (T) and the first glutamine (Q) in the GR DBD sequence (FIG. 1). Translating ribosomes can therefore be made to pause at these flanking codons by blocking charging of either tRNA$^{Thr}$ or tRNA$^{Gln}$. This was done by excluding Thr or Gln from the translation mix and by using tRNA synthetase fractions defective either in ThrRS or GlnRS activity (Material and Methods).

A new technique to translate natural mRNAs, covalently linked to a column matrix, has been applied to $^{14}$C labelling of amino acids T456-G470 (FIG. 1) in the DNA binding domain (DBD) of the glucocorticoid receptor (GR).

Three different translation mixes were prepared (Materials and Methods). The first mix, A, for translation of the N-terminal part of GR DBD contained all amino acids (unlabelled) except Thr and had a defective ThrRS. The second mix, B, for translation of the T456-G470 region contained nine $^{14}$C labelled amino acids, no Gln and was defective in GlnRS activity. The third mix, C, contained all amino acids (unlabelled) and was deficient in release factor RF1 activity. This last mix was used to translate the C-terminal part of GR DBD.

Ribosomes (500 pmol) together with fmet-tRNA$^{fMet}$ and initiation factors were applied to a column (0.4 ml) with mRNA for GR DBD coupled to it (Materials and Methods). Initiation of translation was obtained by 10 min incubation at room temperature. Subsequently, translation mix A was applied to synthesise the fragment M397-L455 (FIG. 1) of GR DBD.

After 5 min incubation with mix A the column was washed with PMGPT buffer (polymix buffer plus 1 mM GTP) and translation mix B was added for synthesis of the labelled peptide region. The column wash after this step was applied to a protein gel (FIG. 2), showing that some small peptide fragments had been eluted (lanes B1, B2) by the rinsing.

The complete GR DBD was synthesised by applying mix C. FIG. 2 shows that the column wash after this step (lanes C1–C3) contained a small amount of GR DBD eluted from the column (lane 2) together with small amounts of short peptides. It was not until after RF1 addition to the column (lane R5), that the dominant fraction of region labelled GR DBD was eluted by washing (lanes R6 and R7). The column wash at this last step contained region labelled GR DBD together with RF1 and no other components. From this point a completely pure product could be obtained in a single gel filtration step separating GR DBD from RF1.

According to band shift assays (not shown) the in vitro synthesised region-labelled DBD was fully active in DNA binding.

To get almost pure region-labelled product (FIG. 2) it was necessary to eliminate the RF1 activity of mix C. This is illustrated in FIG. 4, which shows an experiment where the last translation mix, C, contained a synthetase fraction with fully active RF1. In this experiment we also used $^{35}$S Cys of high specific activity in mixes A, B, and C to make drop-off of peptides visible in the gel (FIG. 3). In this case the full length GR DBD eluted from the column after translation with mix C (lanes C1 and C2), together with all components of that mix. Some S—S bonds were formed between free $^{35}$S Cys and SH-groups of proteins in the translation mixes, so that EF-Tu, which is the main component of the translation mixes, could be seen in the different lanes of FIG. 3. The absence of any full-length GR DBD product in lanes A1–A3 demonstrates that during translation with mix A the ribosomes are indeed stalled at the first Gln codon.

The amount of region-labelled GR DBD produced in these experiments (FIGS. 2, 3) was about 2 pmol, with about 140 pmol of column coupled mRNA (Materials and Methods).

The amount of synthesised region-labelled GR DBD increased almost linearly with the amount of ribosomes applied to the column in the initiation step (FIG. 4). This experiment demonstrates that it is the efficiency of ribosome initiation, rather than the amount of available column-coupled mRNA, that limits the protein yield.

Comments

One advantage of the solid phase technique in the present context is that it greatly facilitates switching between labelled and unlabelled amino acids during translation. An alternative method to prepare region labelled proteins is to translate mRNA in solution and then to purify pausing ribosomes with the nascent peptide by gel filtration. This, more cumbersome, method has also been used to produce region labelled GR DBD (not shown, gel filtration on Sephacryl® S300 HR, Pharmacia Biotech AB). Accordingly the labelling aspect of the invention can be generalised to be carried out with or without the use of solid phases.

Figure 1:
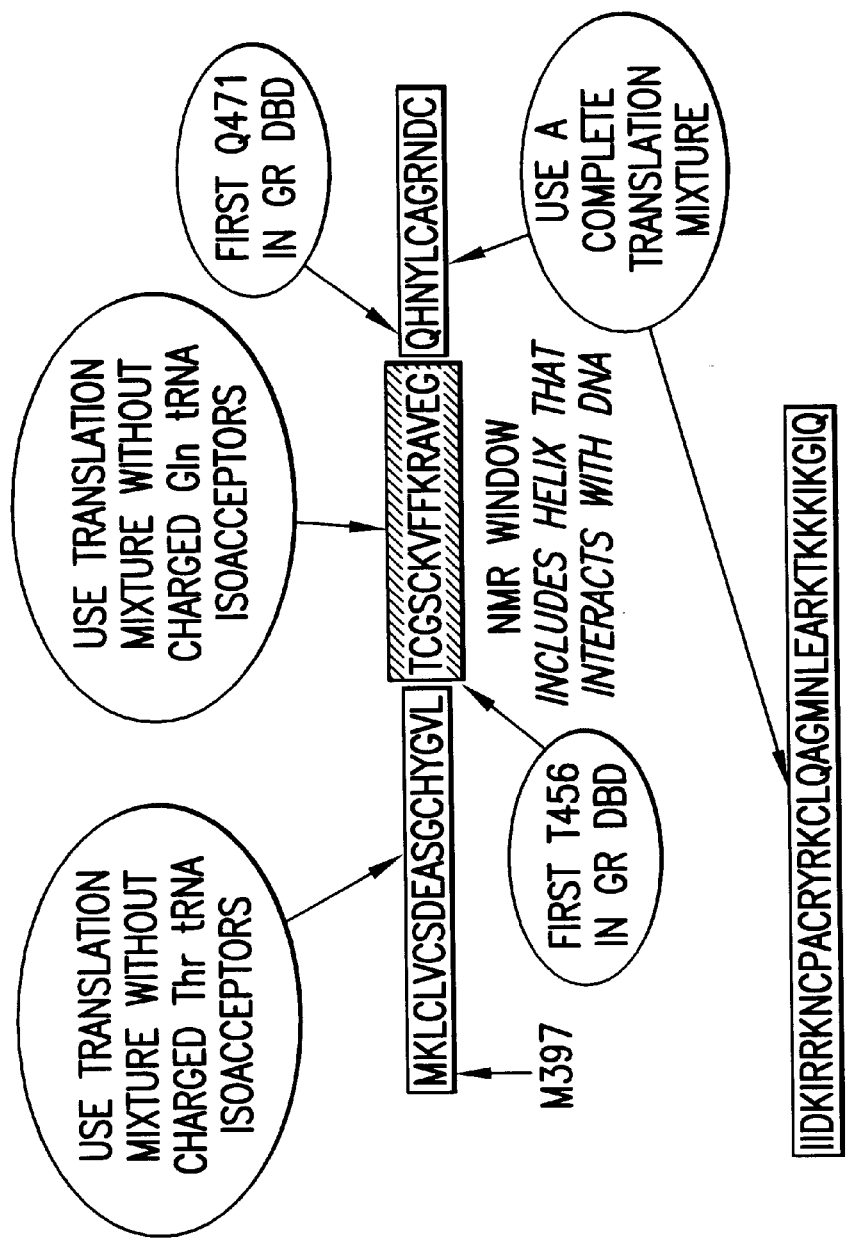
FIG. 1 The amino acid sequence (SEQ ID NO 4 and SEQ ID NO 5) of the glucocorticoid receptor (GR) DNA binding domain (DBD) with the description of the labelling procedure; numbering refer to the rat GR.
Figure 2:
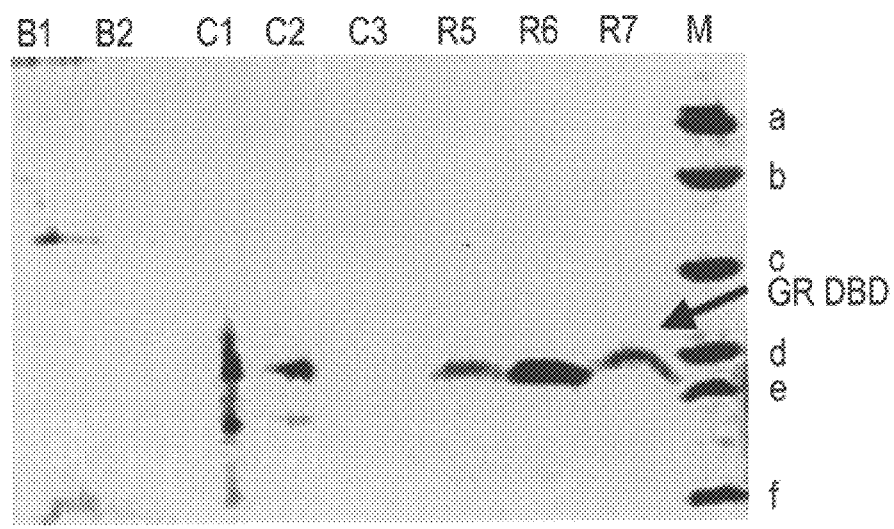
FIG. 2 Synthesis of $^{14}$C-region labelled GR DBD. Elongation was started by adding 0.15 ml of Translation Mix A (TMA) to the column. After 3 min of elongation TMA was removed from the column by washing 5 times with 0.6 ml PMGTP (polymix buffer plus 1 mM GTP). Then 0.15 ml of Translation Mix B, containing nine $^{14}$C-labelled amino acids was added and elongation continued for 5 minutes. After this, 0.45 ml of PMGTP was added and the column eluent was collected (sample B1). The column was subsequently washed four times with 0.6 ml of PMGTP buffer (samples B2–B5). Samples B1–B2 were applied to the gel in lanes B1–B2. Next, we added 0.25 ml of Translation Mix C, allowed 5 min of elongation before adding 0.25 ml of PMGTP after which the column eluent was collected as sample C1. The column was subsequently washed 4 times with 0.6 ml of PMGTP (samples C2–C5). Samples C1–C3 were applied to the gel in lanes C1–C3. Finally, 500 pmol of RF1 in 0.6 ml of PMGTP buffer was added to the column (sample and lane R5). The completed region-labelled GE DBD was eluted from the column by washing with two 0.6 ml volumes of PMGTP buffer (samples and lanes R6 and R7).
Figure 3:
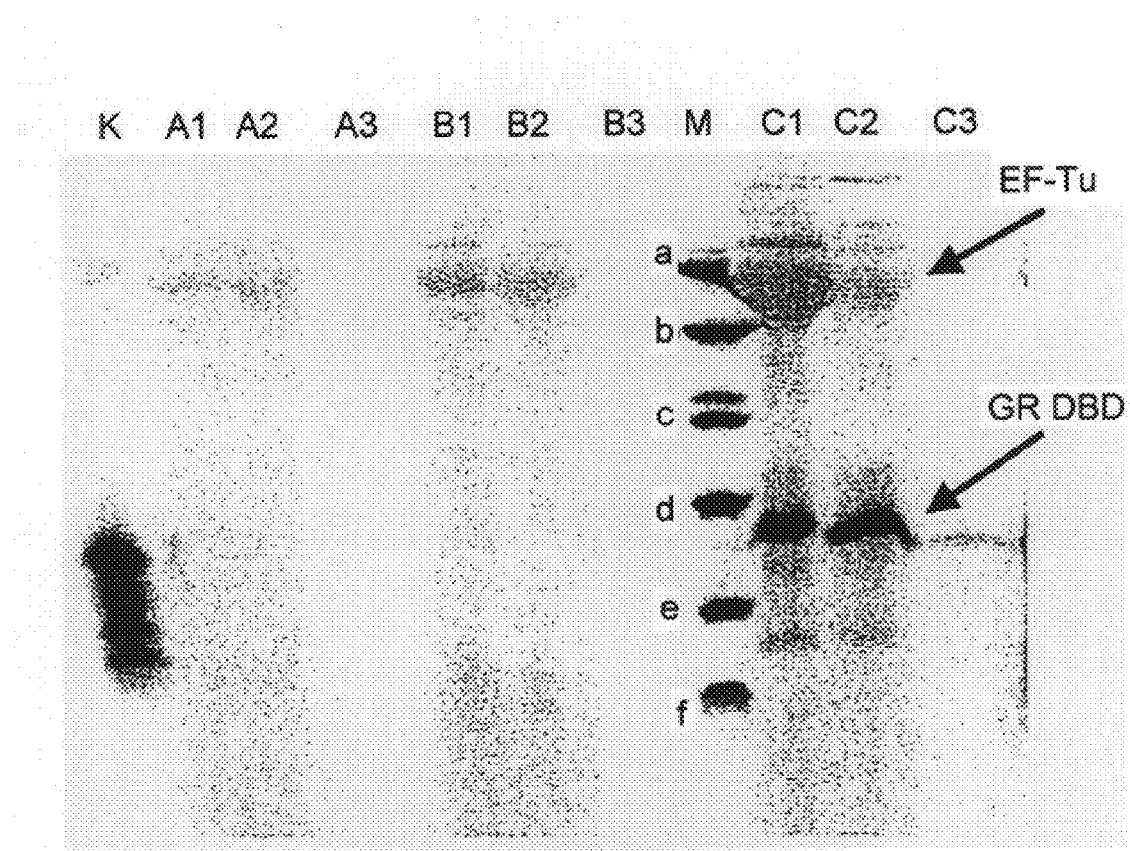
FIG. 3 Synthesis of region labelled GR DBD. Highly radioactive $^{35}$S Cys was added to all translation mixtures to monitor possible drop-off from the ribosomes. Elongation was started by adding 0.15 ml of translation mix A (TMA) to the column. After 3 minutes of elongation 0.45 ml of PMGTP was added and the column eluent collected (sample A1). The column was washed four times with 0.6 ml PMGTP (samples A2–A5). Samples A1–A3 were applied to gel in lanes A1–A3. Lanes B1–B3 correspond to samples B1–B3 from the column after elongation with Translation Mix B (TMB) lacking charged Gln-tRNA isoacceptors. Lanes C1–C3 correspond to samples C1–C3 from the column after elongation with translation mix C (TMC) with native RF1. See the legend to FIG. 2 for more details.
Figure 4:
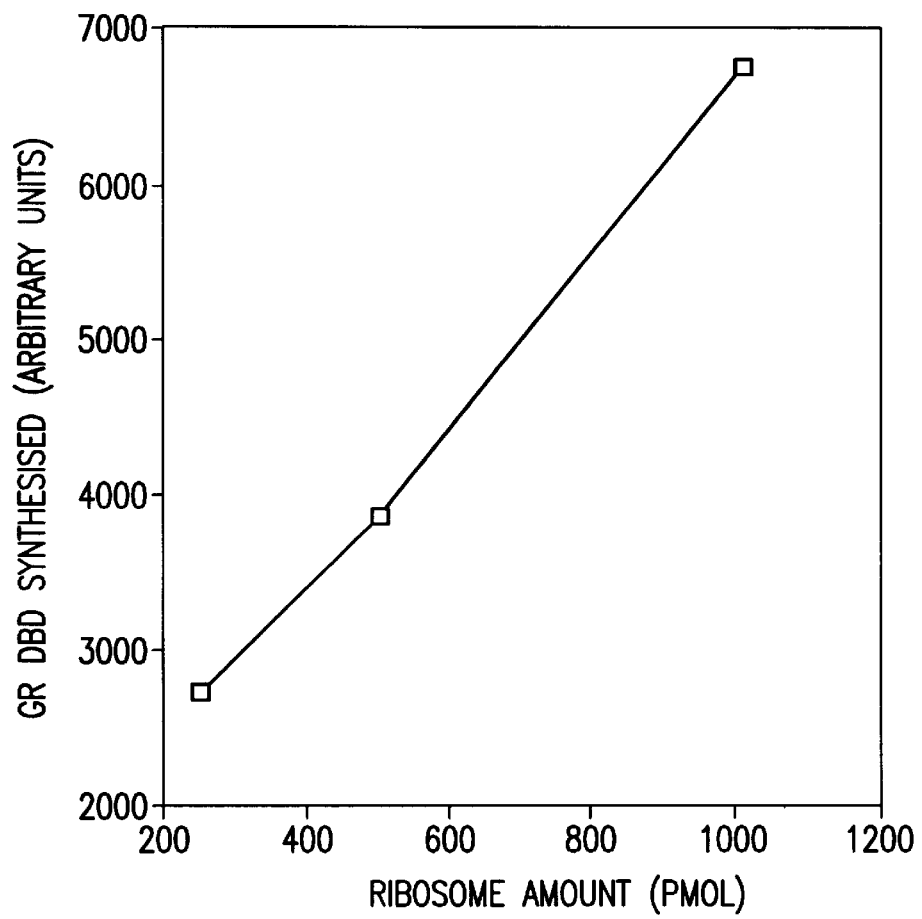
FIG. 4 Dependence of amount of synthesised region labelled GR DBD upon amount of ribosomes used in the initiation step. Amounts of pure GR DBD after each column was calculated from intensities of GR DBD lanes on gel (not shown).

1. REFERENCES:
2. Baranov V L et al., Meth. Enzymol. 59 (1979) 382–397
3. Bax A., Ann. Rev. Biochem. 58 (1989) 223–256
4. Belitsina N V et al. FEBS Lett 57 (1975) 262
5. Belitsina N V et al., Meth. Enzymol. 60 (1979) 745–759
6. Boutillon C et al., Eur. J. Biochem. 231 (1995) 166–180
7. Clore G M et al., Science 252 (1991) 1390–1399
8. Corner et al., J. Med. Biol. 261 (1996) 108–124
9. Dahlman-Wright K et al., J. Biol. Chem. 265 (1990) 14030–14035
10. Dubnoff J S et al., Meth. Enzymol. XX (1971) 248–261
11. Ehrenberg M et al., In: The Practical Approach Series. Ed. Spedding G. IRL Press, Oxford and Washington (1990) 101–129
12. Gold et al., Meth. Enzymol. 185 (1990) 89–91
13. Hård T et al., Science 249 (1990) 157–160
14. Jelenc P C et al., Proc. Natl. Acad. Sci. USA 76 (1979) 3174–3178
15. Jelenc P C., Anal. Biochem. 105 (1980) 369–374
16. Kelmers A D et al., Meth. Enzymol. 20 (1971) 3–9
17. Luisi B F et al., Nature 352 (1991) 572–575
18. Methods in Enzymology, vol 239, "Nuclear Magnetic Resonance, Part C", Academic Press, San Diego (1994)
19. Muchmore D C et al., Meth. Enzymol. 177 (1989) 44–73

20. Olins P et al., J. Biol. Chem. 264 (1989) 16973–16976
21. Pavlov M Yu et al., Arch. Biochem. Biophys. 328 (1996) 9–16
22. Ramesh V et al., Eur. J. Biochem 225 (1994) 601–608
23. Schäagger H et al., Anal. Biochem. 166 (1987) 368–379
24. Soffientini A et al., Prot. Expr. Purif. 5 (1994) 118–124
25. Seno T et al., Biochem. Biophys. Acta 169 (1968) 80–94
26. Wagner E-G H et al. Eur. J. Biochem. 122 (1982) 193–197
27. Wuthrich K., Science 243 (1989) 45–50
28. Zhang H et al. The solution structure of the trp repressor-operator DNA complex. J. Mol. Biol. 238 (1984) 592–614
29. Zang et al., J. Mol. Biol. 242 (1994) 614–618
30. Zengel J-M et al. J. Bacteriol. 129 (1977) 1320–1329

What is claimed is:

1. A method of in vitro production of a protein or polypeptide wherein mRNA encoding said protein or polypeptide is translated, said method comprising:

translating said mMNA when said mRNA is bound to a solid phase; wherein
   a) said translating is paused at one or more predetermined internal codons in the mMNA while maintaining the nascent protein or polypeptide bound in a tRNA-ribosome mRNA complex to said solid phase, and
   b) said translating, up to each of said one or more predetemined internal codons is performed with a translation mix devoid of one or more components necessary to read through the said one or more predetermined internal codons thereby causing said translating to become stalled, and
   c) said translating is restarted by adding a subsequent translation mix containing the factors necessary to read through said one or more predetermined internal codons.

2. The method of claim 1, further comprising d) pausing said translating at a terminating stop codon, said translating up to said terminating stop codon being performed with a translation mix devoid of release factor for said terminating stop codon, thereby causing said translating to become stalled at said terminating stop codon; and
   e) removing said translation mixture used for the translation up to said terminating stop codon from the nascent polypeptide bound in the tRNA-ribosome-mRNA complex to the solid phase; and
   f) adding said release factor so that said nascent polypeptide is released from said tRNA-ribosome-mRNA complex bound to said solid phase.

3. The method of claim 1, wherein said translation mix and said subsequent translation mix differ with respect to the labeling of the amino acids present therein.

4. The method of claim 1, wherein said translating is paused and restarted at two or more of said predetermined internal codons using translation and subsequent translation mixes wherein, i) a subsequent translation mix permits restart of translation at a predetermined internal codon at which translation is paused by a preceding translation mix; and
   ii) a preceding translation mix and a subsequent translation mix differ from each other with respect to one or more labelled amino acids.

5. A method of in vitro production of a protein or polypeptide wherein mRNA encoding said protein or polypeptide is translated, said method comprising:

translating said mRNA when said mRNA is bound to a solid phase; wherein
   a) said translating is paused at a predetermined terminating stop codon, said translating up to said predetermined terminating stop codon being performed with a translation mix devoid of release factor for said predetermined terminating stop codon, thereby causing said translating to become stalled at said predetermined terminating stop codon; and
   b) removing said translation mixture used for the translation up to said predetermined terminating stop codon from the nascent polypeptide bound in the tRNA-ribosome-mRNA complex to the solid phase; and
   c) adding said release factor so that said nascent polypeptide is released from said tRNA-ribosome-mRNA complex bound to said solid phase.

* * * * *